United States Patent
Kalmon et al.

(10) Patent No.: US 9,764,051 B2
(45) Date of Patent: Sep. 19, 2017

(54) MULTI-PANEL STERILIZATION ASSEMBLY WITH TRANSPORT ADHESIVE

(71) Applicant: AVENT, INC., Alpharetta, GA (US)

(72) Inventors: Michael F. Kalmon, Ball Ground, GA (US); Thomas A. Ray, Oshkosh, WI (US); Terry N. Tankersley, LaGrange, GA (US); Joyce V. Lee, Alpharetta, GA (US)

(73) Assignee: Avent, Inc., Alpharetta, GA (US)

( * ) Notice: Subject to any disclaimer, the term of this patent is extended or adjusted under 35 U.S.C. 154(b) by 37 days.

(21) Appl. No.: 14/307,848

(22) Filed: Jun. 18, 2014

(65) Prior Publication Data

US 2015/0367011 A1 Dec. 24, 2015

(51) Int. Cl.
*B65D 65/00* (2006.01)
*A61L 2/26* (2006.01)
*A61B 50/00* (2016.01)
*A61B 50/30* (2016.01)

(52) U.S. Cl.
CPC ............... *A61L 2/26* (2013.01); *A61B 50/30* (2016.02); *A61B 2050/0067* (2016.02); *A61B 2050/0076* (2016.02); *A61B 2050/0079* (2016.02); *A61B 2050/0083* (2016.02); *A61B 2050/0084* (2016.02); *A61B 2050/314* (2016.02); *A61L 2202/10* (2013.01); *A61L 2202/181* (2013.01)

(58) Field of Classification Search
CPC ...... A61L 2/26; A61L 2202/24; A61B 19/026
See application file for complete search history.

(56) References Cited

U.S. PATENT DOCUMENTS

| | | | | |
|---|---|---|---|---|
| 3,680,772 A | * | 8/1972 | Hoover | A61B 19/045 206/438 |
| 3,746,152 A | * | 7/1973 | Allen | A61B 19/045 206/299 |
| 4,011,944 A | * | 3/1977 | Cooley | A61B 19/0256 206/370 |
| 4,342,392 A | * | 8/1982 | Cox | A61B 19/08 128/855 |
| 4,801,480 A | * | 1/1989 | Panza | A61F 13/58 428/354 |

(Continued)

FOREIGN PATENT DOCUMENTS

| | | |
|---|---|---|
| WO | WO 2011/016006 A2 | 2/2011 |
| WO | WO 2013/046186 A1 | 4/2013 |
| WO | WO 2013/046187 A2 | 4/2013 |

OTHER PUBLICATIONS

International Search Report and Written Opinion for PCT/US2015/035975 dated Sep. 24, 2015, 10 pages.

*Primary Examiner* — Derek Battisti
(74) *Attorney, Agent, or Firm* — Dority & Manning, P.A.

(57) ABSTRACT

The multi-panel sterilization assembly includes a barrier panel formed of permeable material having barrier properties, side wings that can include grip portions for folding or unfolding the barrier panel; and a fold protection panel. The assembly has at least one pull tab attached to an end of the barrier panel to aid in unfolding the assembly after sterilization. At least one wing and/or pull tab is held in place against the barrier panel during manufacturing with a transient adhesive that loses strength such that the wing or pull tab is easily pulled off the barrier panel after sterilization.

9 Claims, 2 Drawing Sheets

(56) References Cited

U.S. PATENT DOCUMENTS

| | | | |
|---|---|---|---|
| 5,035,687 A * | 7/1991 | Sandbank | A61F 13/023 |
| | | | 128/DIG. 26 |
| 5,151,092 A | 9/1992 | Buell et al. | |
| 5,196,000 A | 3/1993 | Clear et al. | |
| 5,635,134 A | 6/1997 | Bourne et al. | |
| 6,006,985 A | 12/1999 | Hawkins | |
| 6,391,260 B1 * | 5/2002 | Davis | A61L 2/14 |
| | | | 206/370 |
| 6,578,348 B1 * | 6/2003 | Banks | A61B 19/026 |
| | | | 53/425 |
| 2001/0036519 A1 | 11/2001 | Bayer | |
| 2003/0045856 A1 | 3/2003 | Couture et al. | |
| 2005/0163654 A1 * | 7/2005 | Stecklein | A61B 19/0262 |
| | | | 422/28 |
| 2011/0033137 A1 * | 2/2011 | Gaynor | A61B 19/026 |
| | | | 383/105 |
| 2012/0202000 A1 | 8/2012 | Bricker et al. | |
| 2013/0001283 A1 * | 1/2013 | Friderich | B65D 65/06 |
| | | | 229/87.01 |
| 2013/0081355 A1 | 4/2013 | Gaynor et al. | |
| 2013/0092724 A1 * | 4/2013 | Gaynor | A61L 2/26 |
| | | | 229/87.05 |
| 2014/0224412 A1 * | 8/2014 | Lange | A61F 13/15756 |
| | | | 156/226 |

* cited by examiner

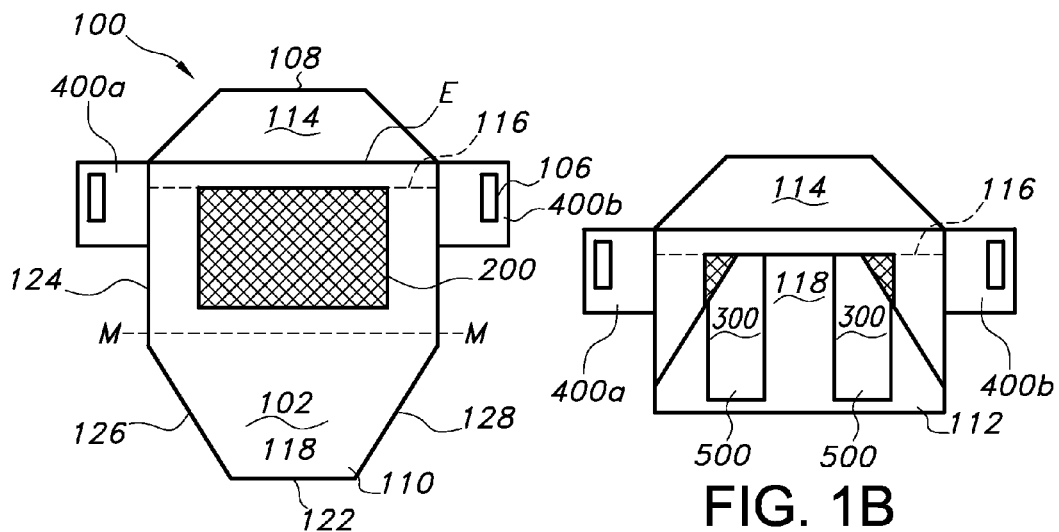
FIG. 1A
FIG. 1B
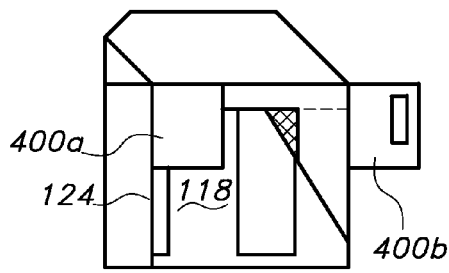
FIG. 1C
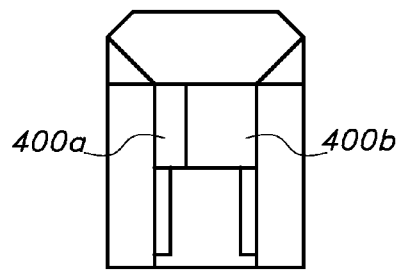
FIG. 1D
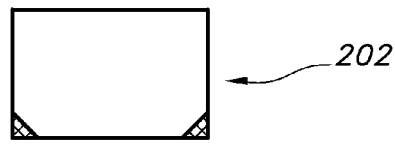
FIG. 1E

MULTI-PANEL STERILIZATION ASSEMBLY WITH TRANSPORT ADHESIVE

The present disclosure relates in general to disposable wraps used to contain content to be sterilized and store that content aseptically until use.

Conventional disposable sterilization wrap is a flat, featureless sheet of material that may occasionally contain one or more additional layers of material for strength or absorbency. For example, U.S. Pat. No. 5,635,134 to Bourne, et al. discloses a multi-ply sterilization wrap which is formed by joining one or more sheets of sterilization wrap (e.g., two separate sheets or one sheet folded over) together to form two similarly sized, superposed panels that allow convenient dual wrapping of an article. As another example, U.S. patent application publication 2001/0036519 by Robert T. Bayer discloses a two ply sterilization wrap that is formed of a single sheet of sterilization wrap material which is folded to form two similarly sized, superposed panels that are bonded to each other. As yet another example, U.S. patent application publication 005/0163654 by Stecklein, et al. discloses a sterilization wrap material that has a first main panel and a second panel that is smaller than the main panel. The second panel is superposed and bonded to the central portion of the main panel such that it is contained entirely within the main panel to reinforce the main panel and/or provide additional absorbency.

US patent application publication 2013/0081355 to Gaynor et al. provides an assembly, package or system that reduces the amount of sterilization wrap material needed for the sterile processing of an instrument tray or article and eliminates the need to grasp the sterilization wrap material to unfold wrap. This assembly has wings on the sides that are used to hold the assembly together once an article is wrapped with the assembly and pull tabs on an end to aid in unwrapping the sterilized article. This assembly reduces the amount of sterilization fabric that can be used in an extended or enhanced steam or heat sterilization process, and that simplifies the task of unwrapping a sterilized instrument tray or article while reducing or avoiding the likelihood that the sterilization fabric will fold back onto itself during unwrapping. It has been found, however, that the pull tabs and wings can move during the process of fabricating the assembly and cause problems in the manufacturing process. This movement can lead to shifting on the assembly line with parts of the assembly catching on equipment and disrupting production. Also, the pull tabs and wings can fall away from the main body of the wrap when in a prewrapping position in the hospital. Before the trays are wrapped, the sterilization wrap is sometimes draped over a bar, ready to be picked up by the user to wrap the sterilization tray or basket. In this pre-wrapping position if the wings and especially the pull tabs are loose, they drape downwards, where they could potentially hit the floor.

It would be useful to have a sterilization wrap that did not allow movement of the pull tabs or wings during manufacturing but did allow the tabs and wings to move freely so that they could be pulled and the wrap opened after manufacturing without causing tears or fibers loosening from the surface.

SUMMARY OF THE DISCLOSURE

The problems described above are addressed by the present disclosure which encompasses a multi-panel sterilization assembly with a barrier panel having at least one pull tab permanently attached to it on one end and the length of the pull tab held against the barrier panel during manufacturing with a transient adhesive. The wings may be held in the same way. The pull tabs are used to unfold the sterilization assembly after it has been folded over an article and it has been sterilized. The transient adhesive is only needed during the manufacturing process, so it loses strength thereafter and the length of the pull tabs and/or wings are easily pulled off of the barrier panel after sterilization of the assembly.

DESCRIPTION OF THE DRAWINGS

The present disclosure will be better understood by reading the Detailed Description of the Disclosure with reference to the accompanying drawing figures, in which like reference numerals denote similar structure and refer to like elements throughout, and in which:

FIGS. 1A through 1E are illustrations of an exemplary sequence of folding an exemplary disposable flexible multi-panel sterilization assembly including side wings and pull tabs having spaced apart pull locations, prior to sterilization.

FIG. 1A illustrates the completely unfolded assembly with the content (or item) to be sterilized.

FIG. 1B illustrates the folding upwardly of the bottom end of the assembly, substantially covering the item to be sterilized.

FIG. 1C illustrates the folding over of the left side of the assembly, onto the folded bottom end and the item to be sterilized.

FIG. 1D illustrates the folding over of the right side of the assembly, onto the folded bottom end and the item to be sterilized.

FIG. 1E illustrates the folding over of the top end of the assembly, onto the folded bottom end and sides as well as the content to be sterilized, to make a package.

FIG. 2A illustrates the package from FIG. 1E after sterilization.

FIG. 2B illustrates the unfolding of the top end of the assembly, revealing the folded bottom end and sides.

FIG. 2C illustrates the unfolding of the right side of the assembly, revealing part of the folded bottom end.

FIG. 2D illustrates the unfolding of the left side of the assembly, revealing the rest of the folded bottom end.

FIG. 2E illustrates the completely unfolded assembly and the item, after sterilization.

DETAILED DESCRIPTION

Figure 2A:
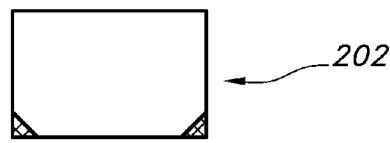
FIGS. 2A to 2E are illustrations of an exemplary sequence of unfolding an exemplary disposable flexible multi-panel sterilization assembly including side wings and pull tabs having spaced apart pull locations.

As used herein, the term "disposable" refers to a product that is so inexpensive that it may economically be discarded after only a single use. Products that are "disposable" are typically intended for single use. The term "single-use" refers to a product that is intended to be used for only once and is not intended to be re-used, re-conditioned, restored or repaired after that use. These products offer advantages in clinical settings by reducing the potential for contamination or infection. In addition, these products can enhance work flow since they are not collected and assembled for reprocessing and reuse.

As used herein, the term "multi-panel sterilization assembly" or "sterilization assembly" or "assembly" refers to a flexible article composed of fabric(s) and/or flexible material(s) that is wrapped around, folded around or otherwise encloses a non-sterile article or non-sterile content prior to sterilization. A sterilization assembly has multiple panels and/or sections providing specific physical properties, functional characteristics and/or structure that provide advantages for wrapping or folding, handling, strength, sterilization, storage after sterilization, and/or unwrapping or unfolding.

As used herein, the term "nonwoven" refers to a web or fabric that has a structure of individual fibers or filaments which are interlaid, but not in an identifiable repeating manner. Nonwovens have been, in the past, formed by a variety of processes known to those skilled in the art such as, for example, meltblowing, spunbonding and bonded carded web processes.

A typical sterilization tray with the dimensions of 10 inches (25.4 cm) by 20 inches (50.8 cm) by 5 inches tall (12.7 cm) typically requires a square piece of sterilization fabric having each side measuring 45 inches for wrapping and sterile processing. This large size piece is needed so that the corner of the fabric can be folded all the way across the top of the tray with some additional excess material so that the preparer of the tray feels confident that the contents are covered and that the piece of fabric will stay down and not spring back. Using a 45 inch, square piece of fabric means that 2025 square inches of material (approximately 13,064 square centimeters) is being used to enclose a tray with a surface area of just 700 square inches (approximately 4,516 square centimeters). In other words, this traditional method requires almost three square inches of material to cover every square inch of a tray of surgical instruments.

The multi-panel sterilization assembly includes a barrier panel formed of permeable material having barrier properties, side wings that can include grip portions for folding or unfolding the barrier panel; and a fold protection panel. The barrier panel has a first end and a second end opposite the first end, a first edge and a third edge, each such edge being generally perpendicular to the first end, and a midpoint to generally delineate the barrier panel into a content receiving region extending from approximately the first end to the midpoint and a content covering region extending from the midpoint to approximately the second end. The assembly has pull tabs that are attached to the second end and positioned to be accessible during the final steps of unfolding or unwrapping a wrapped package. The side wings are desirably located between the first end and the midpoint of the barrier panel and at or near the first edge and the third edge. The fold protection panel is in juxtaposed communication with the barrier panel such that after folding the content covering region and the first and third edges over the content receiving region, the fold protection panel covers them.

The flexible multi-panel sterilization assembly has a barrier panel made with a permeable sheet material having barrier properties: the barrier panel includes a first surface and a second opposing surface, a first end and a second end opposite the first end, a first edge and a third edge, each such edge being generally perpendicular to the first end. The second edge is generally opposite the first end. The barrier panel has a maximum width that is the distance from the first edge to the third edge and a maximum length that is the distance from the first end to the second end. The barrier panel has a midpoint along the length and extending between the first edge and the third edge to generally delineate the barrier panel into a content receiving region extending from approximately the first end to the midpoint and a content covering region extending from the midpoint to approximately the second end.

The assembly has side wings located between the first end and the midpoint of the barrier panel and at or near the first edge and the third edge. The side wings include grip portions for folding or unfolding the barrier panel. The assembly has a fold protection panel in juxtaposed communication with the barrier panel. The fold protection panel is made with a permeable sheet material and includes a proximal end generally adjacent the first end of the barrier panel, a distal end generally opposite the proximal end and at least a first edge and a second edge extending away from the proximal end. The fold protection panel has a maximum width that is the greatest distance from the first edge to the second edge and a maximum length that is the distance from the proximal end to the distal end such that after the barrier panel has been folded at or near the barrier panel's midpoint so the barrier panel's second end is brought towards its first end and the side wing on the first edge and the side wing on the third edge are folded over the barrier panel towards or overlapping each other to form at least a partial enclosure. The distal end of the fold protection panel is configured to cover at least the first edge and the third edge of the folded barrier panel.

Referring now to FIGS. 1A through 1E, there is illustrated an example of a multi-panel sterilization assembly in an exemplary sequence of folding prior to sterilization. FIG. 1A illustrates a multi-panel sterilization assembly 100 composed of barrier panel 102 which cooperates with the fold protection panel 108 and the panel attachment means 106 on the wings 400 on the first surface 110 so the barrier panel 102 can be folded around the content 200 to form a package (such as the package 202 generally illustrated in FIGS. 1E and 2A). The barrier panel 102 is the portion of the flexible multi-panel sterilization assembly 100 that contacts and covers the content 200.

As generally illustrated in FIG. 1B, the second end 118 of the barrier panel 102 is folded up at the midpoint "M" and the second edge 122 brought towards the first end 114 so part of the barrier panel 102 extends over the content 200. As shown in FIG. 1B, the width of the barrier panel at the second end 118 is less than the width of the barrier panel at the first end 114. This provides a configuration of the fourth edge 126 and the fifth edge 128 that allows access to the panel attachment means 106 after the second end 118 is brought up to the first end 114.

A pull tab system 300 and spaced apart pull locations 500 extend from the second end 118 so that the pull tab system 300 is positioned to be accessible during the final steps of unfolding or unwrapping a wrapped package. The pull tab system 300 desirably extends from or is joined to the second end 118 of the barrier panel on the second opposing surface 112 of the barrier panel 102. It is contemplated that the pull tab system 300 may be unitary or integral with the barrier panel. The distal end (i.e., the loose end) of the pull tab system 300 is secured to the barrier panel with a transient adhesive such that the pull tab system 300 does not flop around during wrapping and is in an appropriate position during unwrapping. In particular, the assembly 100 is manufactured with the pull tabs 300 on the lower side of the assembly 100 so the tabs 300 can hang down from the assembly 100 during its progress along the assembly line. Securing the tabs 300 to the assembly 100 is important to keep the tabs from catching on equipment during manufacturing. Similarly, the wings 400 can hang down from the assembly 100 during manufacturing and so should be secured for the same reason as the tabs.

FIG. 1C illustrates the third edge 124 of the barrier panel 102 is folded over the second end 118 (after the second end 118 is brought up to the first end 114). While not necessarily shown to scale, the third edge 124 of the barrier panel 102 after folding need not extend very far toward the middle of the assembly. FIG. 1C illustrates that the side wing 400a on the third edge 124 is deployed so that the panel attachment means 106 (not visible in FIG. 1C) is used to securely place the third edge against the second end 118 of the barrier panel (i.e., the content covering region).

FIG. 1D shows that the first edge 120 of the barrier panel 102 is folded over the second end 118 (after the second end 118 is brought up to the first end 114). FIG. 1D illustrates that the side wing 400b on the first edge 120 is deployed so that the panel attachment means 106 (not visible in FIG. 1D) is used to securely place the first edge against the second end 118 of the barrier panel (i.e., the content covering region).

As can be seen in FIG. 1D, the panel attachment means 106 are positioned on the side wings 400 so they attach to the second end 118 of the barrier panel (i.e., the content covering region) between the spaced apart pull locations 500 of the pull tab system 300. FIG. 1E illustrates that the first end 114 of the barrier panel 102 is folded over the second end 118. While not necessarily shown to scale, the first end 114 of the barrier panel 102 upon folding need not extend very far toward the middle of the assembly. Accordingly, it is evident that the third edge 124 and the first edge 120 generally do not overlap. Unlike conventional sterilization wrap in which the edges are intentionally overlapped, the edges 120 and 124 of the barrier panel are separated by a distance. This difference highlights the importance of the panel attachment means 106 to hold the folded edges 120 and 124 of the barrier panel 102 in place about the content. Moreover, having these edges generally exposed highlights the importance of the fold protection panel 108.

Referring again to FIGS. 1A, 1D and 1E, the fold protection panel 108 and the portion of the barrier panel 102 between the extremity "E" at the first end 114 of the barrier panel and the pre-determined fold line 116 is folded over bringing the first end 114 of the fold protection panel 108 over the second end 118 of the barrier panel. In some embodiments, a portion of the material adjacent the first edge 120 and the third edge 124 may be visible. With this configuration, the actual edges 120 and 124 of the barrier panel 102 are fully covered so the edges themselves are less susceptible to being accidently pulled open or breached during normal handling of the package. The fold protection panel is typically secured utilizing conventional tape that is used with sterilization wrap. Desirably, the fold protection panel covers the edges of the barrier protection panel after it is folded around the content to be sterilized to form a package. The fold protection panel covers these edges to prevent a worker inadvertently opening the folded barrier protection panel. In addition, the fold protection panel shields the edges from snags, pulls or other phenomenon that could impart a peel force to these edges that would cause the panel attachment means to detach. That is, the configuration of the multi-panel sterilization assembly utilizes the fold protection panel to protect exposed edges of the barrier panel after the barrier panel has been folded around content to be sterilized to form a package.

Figure 2B:
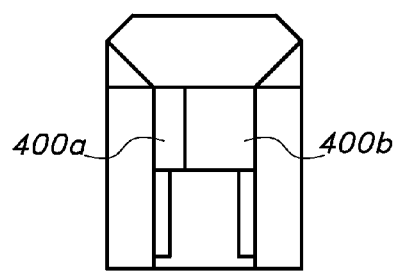
Figure 2C:
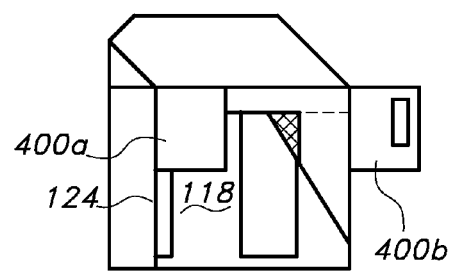
Figure 2D:
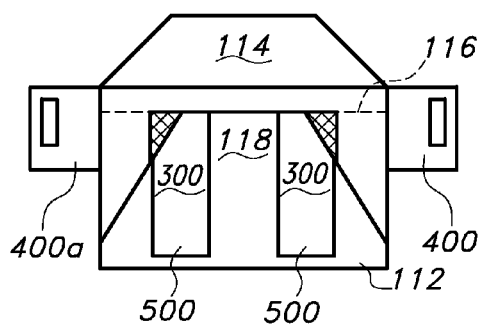

The sequence of unfolding the multi-panel sterilization assembly after it has wrapped around a tray or article and sterilized is generally the reverse of the folding sequence as generally illustrated in FIGS. 2A through 2E. For example, FIG. 2A illustrates a package 202 ready to be unwrapped or unfolded. A conventional tape securing the fold protection panel 108 is broken and the fold protection panel 108 is pulled back to expose the side wings 400 as illustrated in FIG. 2B. The side wings 400 may be pulled up and to the side (away from the center) to detach the panel attachment means such that the first edge 120 and the third edge 124 are unfolded to a configuration as generally illustrated by FIG. 2D. This step may be carried out by pulling the side wings 400 simultaneously or sequentially as shown in FIG. 2C. Importantly, the location/position of the side wings 400, the ability to grip the side wings without compromising sterility, and the leverage and distribution of forces provided by the extended side wings help the fold protection panel, and the first edge 120 and the third edge 124 of the barrier panel remain in a generally flat, unfolded configuration, which keeps them from folding back up over the content 200.

Figure 2E:
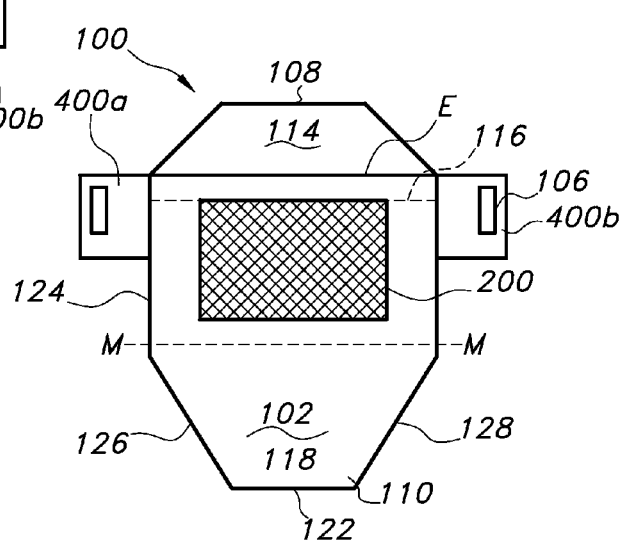

As seen in FIG. 2D, unfolding the side wings 400 exposes the spaced apart pull locations 500 of the pull tab system 300. Each pull location 500 is grasped at a convenient location or at the position when the pull tab system 300 is secured to the barrier panel with an adhesive tab or sticker and the tab or sticker is pulled up. The pull tab system 300 and the second end 118 of the barrier panel is pulled away from the content 200 as shown in FIG. 2E, resulting in complete access to the content 200. Importantly, the spaced apart pull locations 500 help the first edge 120 and the third edge 124 of the barrier panel remain in a generally flat, unfolded configuration which keeps them from folding back up over the content 200.

According to the present disclosure, the barrier panel may be composed of at least one layer of a breathable nonwoven material. Desirably, the breathable nonwoven material is a laminate composed of a layer of spunbonded filaments, a layer of meltblown fibers, and a layer of spunbonded filaments—also called spunbonded-meltblown-spunbonded material. The method of making these layers is known and described in commonly assigned U.S. Pat. No. 4,041,203 to Brock et al which is incorporated herein in its entirety by reference. The material of Brock et al is a three layer laminate of spunbonded-meltblown-spunbonded layers which is also commonly referred to by the acronym "SMS". The two outer layers of SMS are a spunbonded material made from extruded polyolefin fibers, or filaments, laid down in a random pattern and then bonded to one another. The inner layer is a meltblown layer also made from extruded polyolefin fibers generally of a smaller diameter than the fibers in the spunbonded layers. As a result, the meltblown layer provides increased barrier properties due to it fine fiber structure which permits the sterilizing agent to pass through the fabric while preventing passage of bacteria and other contaminants. Conversely, the two outer spunbonded layers provide a greater portion of the strength factor in the overall laminate. The laminate may be prepared using an intermittent bond pattern that is preferably employed with the pattern being substantially regularly repeating over the surface of the laminate. The pattern is selected such that the bonds may occupy about 5-50% of the surface area of the laminate. Desirably, the bonds may occupy about 10-30% of the surface area of the laminate. Other combinations and variations of these materials are contemplated. As a non-limiting example, the inner layer may contain two meltblown layers such that the material may be called "SMMS".

When the barrier panel is composed of or incorporates SMS material(s), the basis weight of the SMS material(s) may be from 1 ounce per square yard or "osy" which is approximately (33 grams per square meter or "gsm") to about 3 osy (100 gsm). For example, the basis weight of the SMS material(s) may be from 1.2 osy (40 gsm) to about 2 osy (67 gsm). As another example, the basis weight of the SMS material(s) may be from 1.4 osy (47 gsm) to about 1.8 osy (60 gsm). The basis weight may be determined in accordance with ASTM D3776-07. Multiple plies or layers of SMS material may be used to provide basis weights ranging from about 2 osy (67 gsm) to about 5 osy (167 gsm).

The permeability of the sheet material of the barrier panel may range from 25 to about 500 cubic feet per minute (CFM) as characterized in terms of Frazier permeability. For example, the permeability of the sheet material barrier panel may range from 50 to about 400 cubic feet per minute. As yet another example, the permeability of the sheet material of the barrier panel may range from 100 to about 300 cubic feet per minute. Alternatively and/or additionally, the permeability of the barrier panel may range from 25 to about 500 cubic feet per minute (CFM) as characterized in terms of Frazier permeability. For example, the permeability of the barrier panel may range from 50 to about 400 cubic feet per minute. As yet another example, the permeability of the barrier panel may range from 100 to about 300 cubic feet per minute. The Frazier permeability, which expresses the permeability of a material in terms of cubic feet per minute of air through a square foot of area of a surface of the material at a pressure drop of 0.5 inch of water (or 125 Pa), was determined utilizing a Frazier Air Permeability Tester available from the Frazier Precision Instrument Company and measured in accordance with Federal Test Method 5450, Standard No. 191A.

When the barrier panel is composed of or incorporates SMS material(s) that have basis weights ranging from about 1 osy (33 gsm) to about 2.6 osy (87 gsm), the permeability of the barrier panel may be lower than 25 cubic feet per minute. For example, when SMS materials having basis weights ranging from about 1 osy (33 gsm) to about 2.6 osy (87 gsm), the permeability of the barrier panel may range from about 20 cubic feet per minute to about 75 cubic feet per minute when determined generally in accordance with ISO 9237:1995 (measured with an automated air permeability machine using a 38 $cm^2$ head at a test pressure of 125 Pa,—exemplary air permeability machine is TEXTEST FX 3300 available from TEXTEST AG, Switzerland). If multiple plies or layers of SMS material are used to provide basis weights ranging from about 2 osy (67 gsm) to about 5 osy (167 gsm), the permeability of the barrier panel may range from about 10 cubic feet per minute to about 30 cubic feet per minute when determined generally in accordance with ISO 9237:1995.

As disclosed herein, during the manufacturing process the pull tabs and wings can move about, since they are only attached to the assembly at one point. As the assembly moves along the production line, the wings and pull tabs can become entangled in parts of the assembly line and cause disruptions in production. Modern assembly lines for this sort of product generally run at a speed of 600 feet per minute (183 meters/min), so loose material is certainly not to be desired.

The challenge in ending loose wings and tabs during manufacture involves not only holding the wings and tabs in place during manufacturing but making sure that they are usable once the assembly is completed. It has been found that a temporary or "transport" adhesive can be used to hold the wings and tab(s) in positing during manufacturing. This adhesive is "transient" in that it only remains functional in place for a short time. The transfer adhesive has a number of requirements; during assembly of the wrap product the adhesive needs to be able to hold the wing or tab to the body of the product with a transfer adhesive bond of at least about 150 grams force tensile pull and, after sterilization, no sticky residue should be left on the outside of the wrapped package to attract dust, lint, or other airborne particles. It is also desirable that after sterilization, and desirably when the user receives the product, the transfer adhesive bond is minimal, i.e., almost unnoticeable, or less than about 150 grams force tensile pull. Suitable adhesives include Fuller HM 1097 and PHO 3000 from H.B. Fuller company of St. Paul, Minn. The Fuller HM 1097 adhesive remains adhesive at a low strength for a long time, similar to "Post-It®" note type adhesives and allows removal and reapplication many times. The Fuller Smart Grip PHO 3000 is a hot melt adhesive having a relatively low viscosity curve and low adhesive strength. As the adhesive cures, the bonds strengthen at first, but then within ½ to 1 hour the bond strength begins to diminish and continues to diminish until after 1 week reaches close to zero. Heat initiates over-crosslinking in the adhesive as it cools. This adhesive is used, for example, in the bottling industry to hold the correct number of bottles or cans together as a unit, until they can be placed in the package. The material cures very quickly compared to other hot melt adhesives and dries to a single clump, at which time it is easily removed from the cans or bottles. Usually, the customer never notices this dried adhesive clump, as it falls off in the package.

While particular embodiments of the present disclosure have been described herein; it will be apparent to those skilled in the art that alterations and modifications may be made to the described embodiments without departing from the scope of the appended claims.

What is claimed is:

1. A flexible multi-panel sterilization assembly comprising a barrier panel having a first end defining a fold protection panel, a second end, opposing first and third edges, a second edge opposite the first end, opposing first and second wings, wherein the first wing, the second wing, or both include panel attachment means to secure portions of the first edge and the third edge to each other or to a portion of the second end after the barrier panel has been folded at or near its midpoint such that its second end is brought towards its first end, and at least one pull tab attached to the second end used to unfold the barrier panel, wherein the pull tab is held against said assembly with a only transient adhesive that loses strength over time, wherein the transient adhesive holds the pull tab against said assembly with a force of at least about 150 grams force tensile pull during manufacturing of the sterilization assembly, wherein the transient adhesive holds the pull tab against said assembly with a force of less than 150 grams force tensile pull after sterilization of the assembly, wherein the barrier panel includes a first surface configured to cover or contact an item to be sterilized and an opposing second surface, wherein the transient adhesive prevents movement of the pull tab during manufacturing yet allows the pull tab to move freely after manufacturing, wherein movement of the pull tab during manufacturing is prevented utilizing attachment means consisting of the transient adhesive.

2. The sterilization assembly of claim 1, wherein the wings are located on the second surface of the barrier panel.

3. The sterilization assembly of claim 1, wherein the panel attachment means comprise adhesive tape, double-sided adhesive tape, cohesive materials, hook and loop fastening systems, mechanical fastening systems, snaps, clips, magnets, catches, slots and tabs, and combinations thereof.

4. The sterilization assembly of claim 1, wherein the sterilization assembly includes two pull tabs and two spaced apart pull locations.

5. The sterilization assembly of claim 1, wherein the at least one pull tab is positioned to be accessible during unfolding or unwrapping the item after sterilization.

6. The sterilization assembly of claim 5, wherein the pull tab extends from or is joined to the second end of the barrier panel.

7. The sterilization assembly of claim 5, wherein the pull tab extends from or is joined to the second end of the barrier panel at the opposing second surface.

8. The sterilization assembly of claim 1, wherein a distal end of the at least one pull tab is secured to the second end of the barrier panel with the transient adhesive.

9. The sterilization assembly of claim 1, wherein the transient adhesive is a hot melt adhesive.

* * * * *